US00PP12069P2

(12) United States Plant Patent
Huang

(10) Patent No.: US PP12,069 P2
(45) Date of Patent: Aug. 28, 2001

(54) NANDINA PLANT NAMED 'MONUM'

(75) Inventor: Dao Shun Huang, Walnut, CA (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 08/803,123

(22) Filed: Feb. 20, 1997

(51) Int. Cl.[7] ..... A01H 5/00
(52) U.S. Cl. ..... Plt./235
(58) Field of Search ..... Plt./235

(56) References Cited

U.S. PATENT DOCUMENTS

P.P. 5,560 * 9/1985 Rushing ..... Plt./235
P.P. 5,656 * 2/1986 Barr ..... Plt./235
P.P. 5,659 * 2/1986 Barr ..... Plt./235
P.P. 8,530 * 1/1994 Young ..... Plt./235
P.P. 11,453 * 7/2000 Treiber et al. ..... Plt./235

* cited by examiner

*Primary Examiner*—Bruce R. Campell
*Assistant Examiner*—Kent L. Bell
(74) *Attorney, Agent, or Firm*—Klarquist Sparkman Campbell Leigh & Whinston, LLP

(57) ABSTRACT

A new and distinct variety of *Nandina domestica* (Heavenly Bamboo) characterized by leaflets that are narrower and longer than is typical for the species, and a unique, vibrant seasonal foliage coloration. In the spring, the 'Monum' foliage is deep purplish-red turning to dark green in the summer and reddish purple in the winter.

1 Drawing Sheet

The present invention relates to a new and distinct variety of *Nandina domestica,* a member of the Berberidaceae family, commonly known as Heavenly Bamboo. This new 'Monum' variety resulted from a naturally occurring, whole plant mutation discovered in a cultivated planting of the *Nandina domestica* variety 'Compacta' (unpatented). 'Monum' appeared different from 'Compacta' plants growing in #5 nursery containers in Azusa, Calif., and was initially discovered around May 1993. The 'Monum' variety differs from 'Compacta' and other Heavenly Bamboo plants known to the inventor due to its narrower, longer leaf and its unique, vibrant seasonal foliage coloration. In the spring, the 'Monum' foliage is deep purplish-red turning to dark green in the summer and reddish purple in the winter.

*Nandina domestica* 'Monum' has more vibrant seasonal foliage coloration than the parent *Nandina domestica* 'Compacta' or any other known *Nandina domestica* cultivars known to the inventor.

'Monum' has been asexually reproduced by shoot tip culture and cuttings since its discovery in 1993 in Azusa, Calif. However, via extensive asexual propagation of this plant and observation of resulting progeny, it has been proven that the novel, exceptional characteristics of this new variety are fixed, stable, and that the new variety reproduces true to type through asexual propagation.

BRIEF DESCRIPTION OF THE DRAWING

The photographic illustration shows an approximately 2 year old plant of the 'Monum' variety, exhibiting a deep purplish-red new spring foliage contrasting with the deep green mature foliage. Foliage colors in the photographic illustration may appear different from actual foliage colors due to differing light conditions.

DETAILED BOTANICAL DESCRIPTION

The following is a detailed description of my new variety of Heavenly Bamboo, with color terminology in accordance with British Horticultural Colour Charts (copyright 1941, Robert Wilson). Unless otherwise indicated, this description relates to 'Monum' plants about 2 to 2½ years old growing in Azusa, Calif.

Parentage: Naturally occurring, whole plant mutation discovered in a cultivated planting of the *Nandina domestica* variety 'Compacta' (unpatented).

Overall habit: Evergreen shrub, upright unbranched single cane-like stems, light airy foliage composed of leaflets.

Overall size: Like 'Compacta,' with a height of about 1.5 to 2.0 meters tall with a spread of about 1 meter at five years of age. Ultimate size yet unknown.

Stems: Upright, branched, and cane-like. Generally Maroon 1030/3 in color.

Foliage: Overall length of leaflet including petiole from tip of terminal leaflet to attachment to stem 30 to 50 cm long. Leaf structure is divided into 2 to 3 pinnately compound leaflets, typical of 'Compacta'. Mature terminal leaflets of the 'Monum' variety average approximately 1.5 to 2.0 cm longer than mature terminal leaflets of the 'Compacta' variety.

Leaflets:

*Shape.*—Narrow elliptic, slightly recurved; different than the obtuse elliptic leaflet shape typical of leaflets of the 'Compacta' variety. Apex is narrowly acute. Base is attenuate.

*Size.*—Terminal leaflets are about 3.5 to 6.0 cm long and about 1.2 to 1.9 cm wide. Side leaflets are about 2.0 to 3.0 cm long and about 1.0 to 1.2 cm wide.

*Texture.*—Coriaceous, slightly puckered.

*Color.*—New growth foliage of 'Monum' is more purple in color, Maroon 1030/3, compared to the rose color, Delft Rose 020/2 and 020/1, of new growth in the 'Compacta' variety. My new variety does not display the typical rose color of the 'Compacta' variety. Mature growth foliage of 'Monum' plants is a darker green color, Parsley Green 00962, than the Lettuce Green 861 of the 'Compacta' variety. Young leaflets, upper side: Maroon 1030/3. Young leaflets, underside: Maroon 1030/3 with splotches of Parsley Green 00962/3. Intermediate leaflets, upper side: Parsley Green 00962/3 with varying amounts of Maroon 1030/3. Intermediate leaflets, underside: Parsley Green 00962/3 to Fern Green 0862/2 with splotches of Maroon 1030/3. Mature leaflets, upper side: Parsley Green 00962/3 blended with Spinach Green 0960/1. Mature leaflets, underside: Parsley Green 00962/3 blended with Fern Green 0862.

*Margin.*—Entire.

*Venation.*—Pinnate to reticulate. Upper vein color consistent with upper leaf color. Lower vein color consistent with lower leaf color.

*Petiole.*—Typically about 2.0 to 3.0 cm long and about 2 mm in diameter, and Parsley Green 00962 with Maroon 1030/3 in color.

*Size* (*without petiole*).—Leaflets are longer and narrower than typical for 'Compacta'. The terminal leaflet is the larger leaflet compared to the side leaflets. Mature, terminal leaflets of 'Monum' plants range in size from about 3.5 to 6 cm long and about 1.2 to 1.9 cm wide. Typical mature terminal leaflets of the 'Compacta' variety range in size from about 2 to 5 cm long and about 1 to 2.1 cm wide. Mature, side leaflets of 'Monum' plants range in size from about 2 to 3 cm long and about 1 to 1.2 cm wide. Typical mature side leaflets of the 'Compacta' variety range in size from 1.9 to 2.2 cm long and 1.2 to 1.8 cm wide.

Cold hardiness: Like 'Compacta', USDA Zone 6 (−10° F.).

Disease resistance: Not resistant to Cucumber Mosaic virus, but does not exhibit Cucumber Mosaic virus at this time.

Pest resistance: Similar to 'Compacta' variety.

Flower buds: Description based on plants flowering in Azusa, Calif.

*Size.*—About 7 to 10 mm in length and about 3 to 5 mm in diameter.

*Shape.*—Elliptic.

*Color.*—Primrose Yellow 601/3 with Cyclamen Purple 30/3, 30/2, and 30/1 at the base of the bud.

Flowers:

*Petals.*—3 in number. Size: About 6 to 7 mm in length and about 2 to 3 in width. Color: Upper and lower surfaces are Egyptian Buff 407/3. Shape: Broad, elliptic, reflexed. Apex: Acute. Base: Obtuse. Margin: Entire. Texture: Glabrous.

*Stamens.*—6 in number. Anthers sessile. Size: About 4 to 6 mm in length and about 1 to 2 mm in width. Color: Chrome Yellow 605.

*Pistil.*—Hypogynous. Quantity: One. Size: About 5 to 7 mm in length, with a style about 2 to 3 mm in length. Stigma: Peltate. Color: Chartreuse Green 663/2.

*Inflorescence.*—Approxiamtely 150 flowers. Length: About 20 to 30 cm long; usually smaller axillary panicle 5 cm shorter. Diameter: Each panicle is about 5 cm in width; inflorescence ranging from 15 to 20 cm. Type: Terminal panicle. Lastingness of individual bloom: 1 to 2 days.

*Peduncle.*—Size: About 20 to 30 cm in length and about 2 to 4 mm in diameter. Color: Plum Purple 934 and Maroon 1034 with Parsley Green 00962/3. Season: Bloom appears in early spring and into summer. Fragrance: None detected.

*Fruit and seeds.*—None observed.

I claim:

1. A new and distinct Nandina plant named 'Monum', substantially as illustrated and described herein.

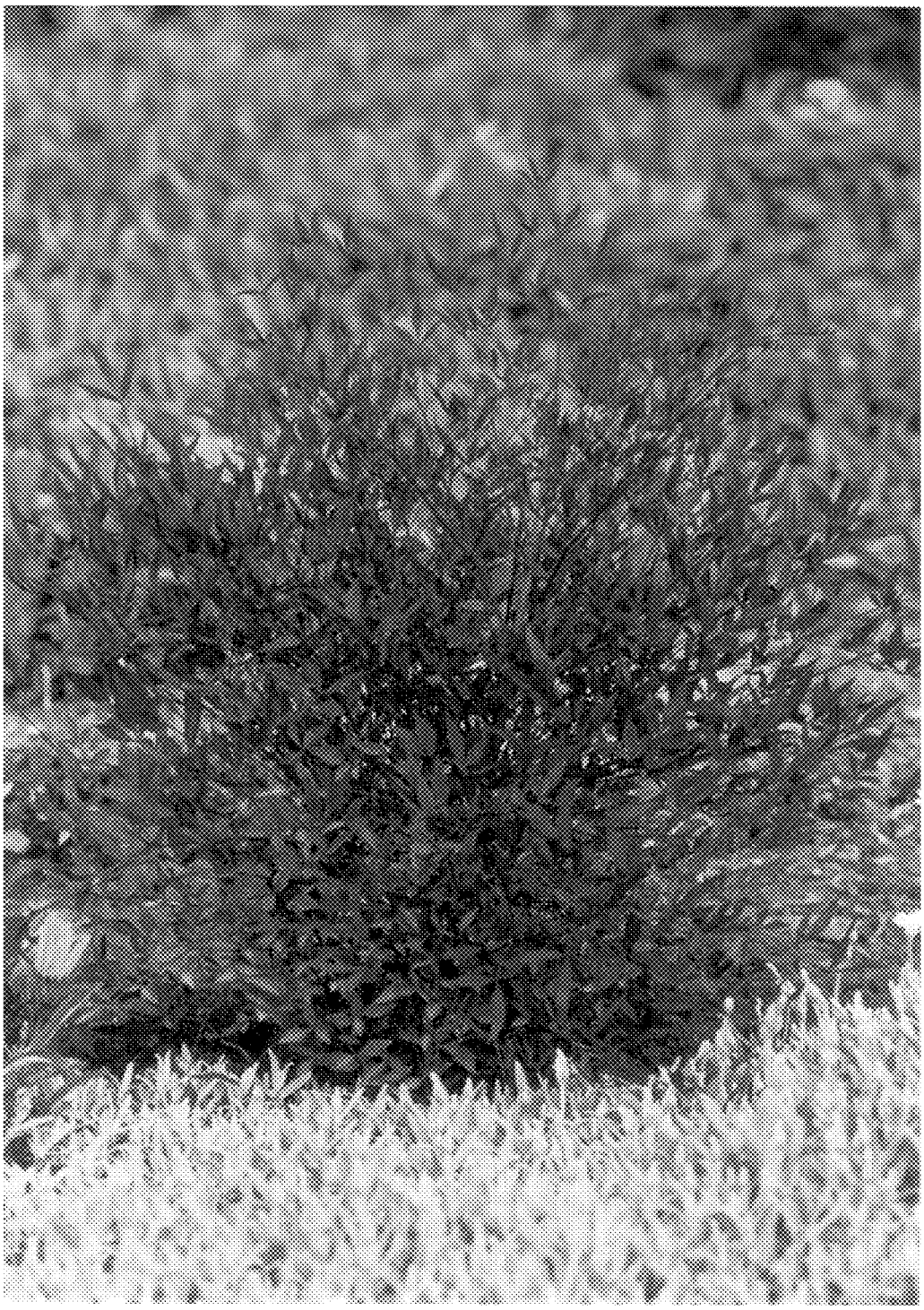

* * * * *